United States Patent
Pendleton et al.

(10) Patent No.: US 9,539,127 B2
(45) Date of Patent: Jan. 10, 2017

(54) URETERAL ENDOLUMINAL ABRASION DEVICE

(71) Applicant: Cook Medical Technologies LLC, Bloomington, IN (US)

(72) Inventors: Steven L. Pendleton, Spencer, IN (US); Steven J. Charlebois, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/136,975

(22) Filed: Dec. 20, 2013

(65) Prior Publication Data
US 2014/0188249 A1    Jul. 3, 2014

Related U.S. Application Data

(60) Provisional application No. 61/746,895, filed on Dec. 28, 2012.

(51) Int. Cl.
*A61M 27/00* (2006.01)
*A61F 2/95* (2013.01)

(52) U.S. Cl.
CPC .............. *A61F 2/95* (2013.01); *A61M 27/008* (2013.01)

(58) Field of Classification Search
CPC ...... A61F 2002/048; A61F 2/95; A61B 17/22; A61B 17/3207; A61B 17/320725; A61B 17/320783
USPC .................................... 600/562; 604/22, 45
See application file for complete search history.

(56) References Cited

U.S. PATENT DOCUMENTS

| | | | |
|---|---|---|---|
| 7,494,497 | B2 | 2/2009 | Weber |
| 8,313,507 | B2 * | 11/2012 | Ravikumar ........ A61B 17/0218 606/205 |
| 2003/0040754 | A1 | 2/2003 | Mitchell et al. |
| 2005/0070888 | A1 | 3/2005 | Dimatteo et al. |
| 2008/0077164 | A1 | 3/2008 | Murphy |
| 2009/0105687 | A1 | 4/2009 | Deckman et al. |
| 2009/0171465 | A1 | 7/2009 | Bucay-Couto et al. |
| 2009/0216319 | A1 * | 8/2009 | Kennedy et al. ............ 623/1.42 |
| 2012/0095545 | A1 | 4/2012 | Yamagata |
| 2012/0157878 | A1 * | 6/2012 | Mendez ........................ 600/562 |

FOREIGN PATENT DOCUMENTS

| | | |
|---|---|---|
| EP | 1872749 | 1/2008 |
| WO | 2008/148385 | 12/2008 |
| WO | 2012/007330 | 1/2012 |

OTHER PUBLICATIONS

Karl Kreder and Roger Dmochowski; 2007, Taylor and Francis Group, The Overactive Bladder: Evaluation and Management; p. 118.*

(Continued)

*Primary Examiner* — Thomas J Sweet
*Assistant Examiner* — Wade P Schutte
(74) *Attorney, Agent, or Firm* — Brinks Gilson & Lione

(57) ABSTRACT

An endoluminal medical device includes a cannula, the cannula having a proximal end and a distal end; an abrasion member having a series of struts interconnected by a series of bent segments forming a plurality of prongs attached to the cannula, the abrasion member having a first section and a second section; where the prongs of the first section of the abrasion member extend radially outward from the cannula.

7 Claims, 7 Drawing Sheets

(56) References Cited

OTHER PUBLICATIONS

Extended European Search Report, EU Patent Application No. 13198360.3, report dated Mar. 20, 2014, 7pp.
Gupta et al., "Prospective Randomized Evaluation of Periureteral Botulinum Toxin Type A Injection for Ureteral Stent Pain Reduction", The Journal of Urology, Feb. 2010, vol. 183, Issue 22, pp. 598-602.

* cited by examiner

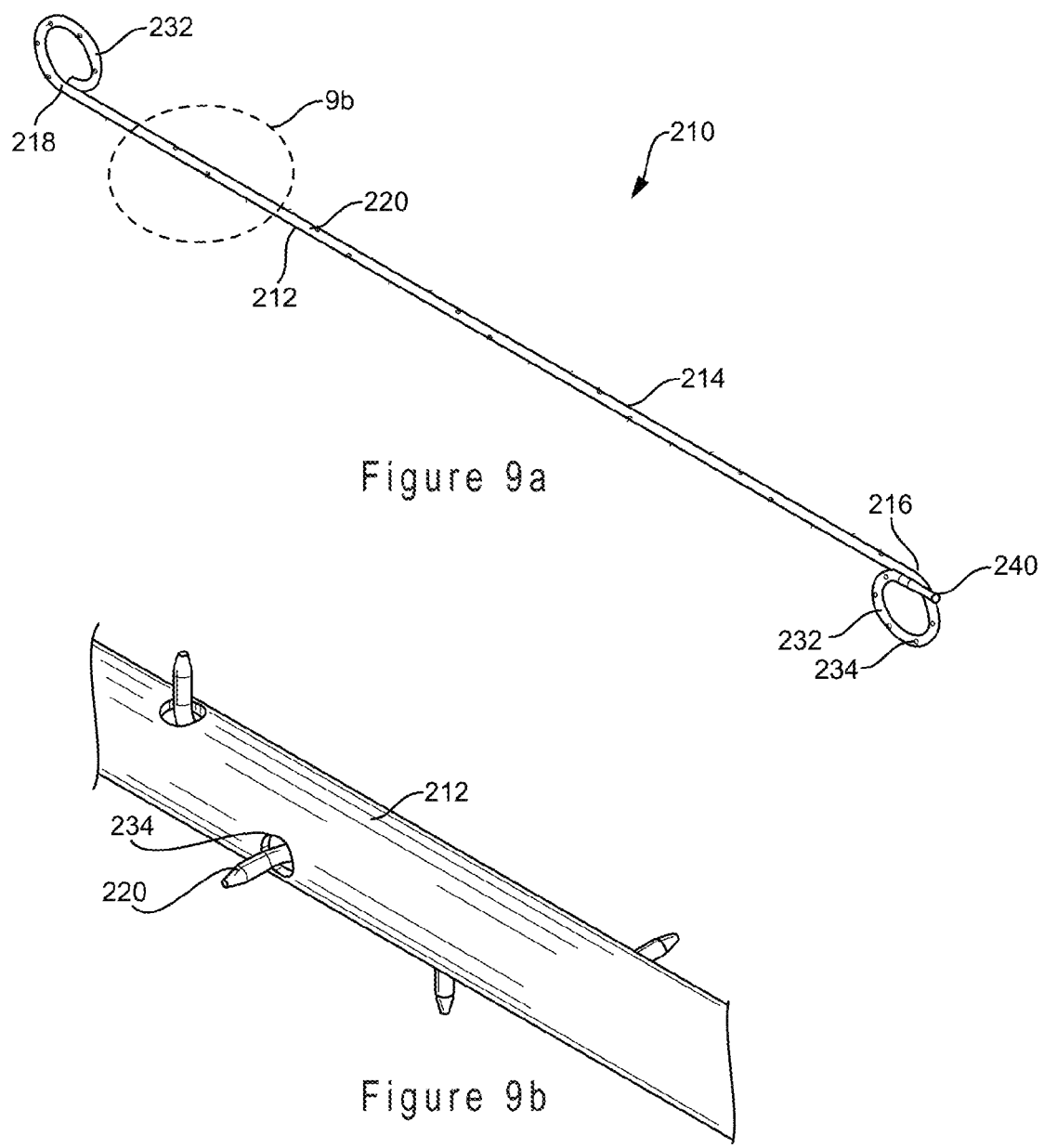

URETERAL ENDOLUMINAL ABRASION DEVICE

RELATED APPLICATIONS

The present application claims priority to U.S. Provisional Patent Application Ser. No. 61/746,895 filed Dec. 28, 2012, the entirety of which is hereby incorporated by reference.

TECHNICAL FIELD

The invention relates generally to medical devices and, particularly, medical devices that can be used in a technique for more readily introducing drug eluting stents useful for urinary drainage.

BACKGROUND

Minimally-invasive surgery has evolved to a point where procedures that were unimaginable a few years ago are now routinely performed on a daily basis. Indwelling ureteral stents have been widely used for years. Such stents are placed in the ureter, which is the duct between the kidney and the bladder, for the purpose of establishing and/or maintaining an open, patent flow of urine from the kidney to the bladder.

Ureteral stents may be used to retain patency of the ureteral lumen and to continue normal urinary drainage following the treatment and removal of stones and calculi from kidneys and ureters. To treat this condition, several individual steps are involved. In one procedure, these steps include placing a relatively narrow wire guide through a urethra and a bladder, and then through the ureter and into the kidney. After the wire guide is placed, a catheter is run along the wire guide, dilating the body passage (the urethra and the ureter) as it moves down the wire guide. The access sheath also dilates the body passages as it moves from outside the body, through the urethra, and into the ureter, down the desired location, and into or very near the kidney.

The physician may then remove calculi and stones through the access sheath, using a grasper, a retrieval basket or other device. The access sheath protects the ureter from repeated passage of the retrieval device while the stones or calculi are removed. After the stones are removed, the ureteral stent may be placed into the ureter through the access sheath, using the catheter or a pushing tube to position the stent.

The typical ureteral stent can be composed of various radiopaque polymers, including polyethylene, silicone, polyurethane, and thermoplastic elastomers. These stents are retained in the ureter by a retentive anchoring portion, such as a curved shape, pigtail, coil, J-shape, or hook configuration, at either end of the stent that engages the walls of the bladder and the kidney, respectively. The stent is resilient to allow it to be straightened for insertion into a body passageway and returned to its predetermined retentive anchoring shape when in situ.

There can be problems, however, with ureteral stents, due to pain and discomfort felt by patients. An attempt to reduce problems associated with pain and discomfort to the patient may be addressed through the introduction of pharmacologically active agents in conjunction with the ureteral stent. However, studies have demonstrated that intravesical drug delivery can be limited by the low permeability of the urothelial layer. As such, the urothelial layer of the ureter may serve as a significant barrier to the introduction of pharmacological active agent into the tissue of the ureter. In addition, more of the pharmacological active agent may elute into the urine of the patient instead of the tissues of the ureter, which limits the effectiveness of the pharmacological active agent within the patient.

BRIEF SUMMARY

In one aspect, an endoluminal medical device includes a cannula, the cannula having a proximal end and a distal end; an abrasion member having a series of struts interconnected by a series of bent segments forming a plurality of prongs attached to the cannula, the abrasion member having a first section and a second section; where the prongs of the first section of the abrasion member extend radially outward from the cannula. In some embodiments, the first section of the abrasion member includes five prongs. In other embodiments, the bent segments of the abrasion member have a generally circular configuration.

In another aspect, an endoluminal medical device, including a tubular housing having a proximal end, a distal end, and a lumen longitudinally disposed therethrough; at least one abrasion member having a series of struts interconnected by a series of bent segments forming a plurality of prongs attached to the tubular housing, the abrasion member having a first section and a second section; where the prongs of the first section of the abrasion member extend radially outward from the housing, and where the bent segments of the prongs of the first section are configured to engage with the urothelium of the ureter. In some embodiments, the abrasion member comprises a shape-memory material.

In yet another aspect, a stent for placement in the ureter, includes a tubular housing having a proximal end, a distal end, and a lumen longitudinally disposed therethrough; at least one abrasion member positioned on the tubular housing; where at least a portion of the abrasion member extends radially outward from the housing and is configured to engage with the urothelium of the ureter. In some embodiments, the first section of the abrasion member comprises five prongs.

In still another aspect, a method of introducing an abrasion to the urothelium layer of the ureter includes providing an endoluminal medical device, the endoluminal device having a tubular housing having a proximal end, a distal end, and a lumen longitudinally disposed therethrough; at least one abrasion member having a series of struts interconnected by a series of bent segments forming a plurality of prongs attached to the tubular housing, the abrasion member having a first section and a second section; where the prongs of the first section of the abrasion member extend radially outward from the housing introducing the endoluminal device into the ureter; and the urothelium layer of the ureter with the endoluminal device.

BRIEF DESCRIPTION OF THE DRAWINGS

FIG. 9a depicts an alternative embodiment of an endoluminal device having an abrasion member.

FIG. 9b depicts a portion of the endoluminal device of FIG. 9.

DETAILED DESCRIPTION OF THE DRAWINGS AND THE PRESENTLY PREFERRED EMBODIMENTS

Figures 1, 2:
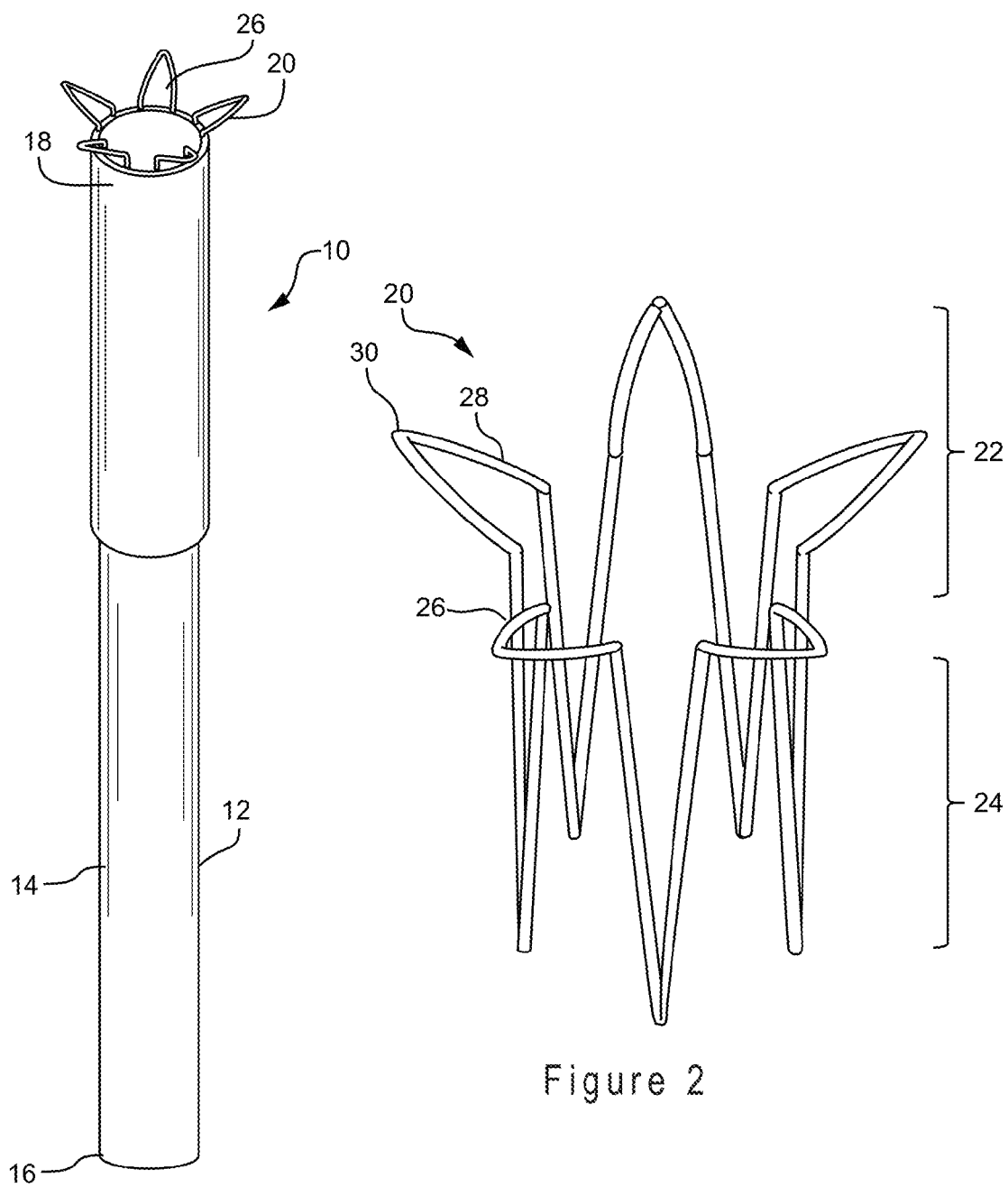
FIG. 1 depicts an embodiment of an endoluminal medical device disposed having an abrasion member.
FIG. 2 depicts a view of an abrasion member for use with the endoluminal medical device of FIG. 1.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The terms "about" or "substantially" used with reference to a quantity includes variations in the recited quantity that are equivalent to the quantity recited, such as an amount that is insubstantially different from a recited quantity for an intended purpose or function.

The term "prosthesis" means any device for insertion or implantation into, or replacement, for a body part or function of that body part. It may also mean a device that enhances or adds functionality to a physiological system. The term prosthesis may include, for example and without limitation, a stent, stent-graft, filter, valve, balloon, embolization coil, and the like.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include, without limitation, urethral and ureteral passages, blood vessels, respiratory ducts, gastrointestinal ducts, such as the biliary duct, intestines, the esophagus, the pericardial cavity, the thoracic cavity, and the like. Accordingly, the terms "endoluminal device" or "endoluminal prosthesis" describe devices that can be placed inside or moved through any such lumen or duct.

The terms "patient," "subject," and "recipient" as used in this application may refer to any animal, particularly humans.

The terms "proximal" and "distal" will be used to describe opposing axial ends of the ureteral stent, as well as the axial ends of various component features. The term "proximal" is used to refer to the end of the ureteral stent (or component thereof) that is closest to the operator during use of the system. The term "distal" is used to refer to the end of the ureteral stent (or component thereof) that is initially inserted into the patient, or that is closest to the patient during use.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "medical device" means any object that is itself or that includes a component that is intentionally inserted into the body of a patient as part of a medical treatment, and that comprises a structure adapted for introduction into a patient. The medical device can be a tool, such as, without limitation, a catheter, a wire guide, a forceps, or a scissors used to affect a surgical procedure at and/or deliver a second medical device to a treatment site in a patient. An alternative medical device of the present invention is one that is commonly intended to be a temporary or permanent implant, such as a stent.

The term "implantable" refers to the ability of a medical device to be positioned, partially or wholly, at a location within a body of a human or veterinary patient for any suitable period of time, such as within a vessel. Implantable medical devices can include devices configured for bioabsorption within a body during prolonged period of time.

The term "controlled release" refers to the release of a material, such as a pharmacologically active ingredient, at a predetermined rate. A controlled release may be characterized by a drug elution profile, which shows the measured rate that the material is removed from a material-containing device in a given solvent environment as a function of time. A controlled release does not preclude an initial burst release associated with the deployment of the medical device. The release may be a gradient release in which the concentration of the material released varies over time or a steady state release in which the material is released in equal amounts over a certain period of time (with or without an initial burst release).

The term "pharmacologically active ingredient" refers to any agent that produces an intended therapeutic effect on the body to treat or prevent conditions or diseases.

A more detailed description of the embodiments will now be given with reference to FIGS. 1-9b. The present invention is not limited to those embodiments illustrated; it specifically contemplates other embodiments not illustrated but intended to be included in the claims.

FIG. 1 discloses an embodiment of an endoluminal medical device 10. In this embodiment, the endoluminal medical device 10 is a cannula 12 comprises a generally tubular body 14 having a proximal end 16, and a distal end 18. The cannula 12 may be made from solid rod or from hollow tubing. The cannula 12 may be composed of any medical grade material having strength suitable for introduction to the site from which an object is to be retrieved, and having a configuration designed for secure grasping, containment and/or removal of the object. Examples of suitable materials including, but are not limited to, metal such as stainless steel or Nitinol, polymeric or plastic materials having fibrous or particulate fillers incorporated in them such as nylons, polycarbonates, polytetrafluoroethylene, and any other reinforced or un-reinforced plastic material suitable for the application. The cannula 12 may have a length and an outer diameter sufficient to extend through a working channel of medical scope (see FIG. 4), for which the cannula 12 may be removeably positioned. For example, cannula may have an outer diameter of about 6 to 7 French in order to fit within the working channel. Cannula 12 also may comprise a hydrophilic coating (not shown) overlying its outer surface. The hydrophilic coating, when applied to the outer surface of cannula, imparts suppleness and kink resistance to the cannula. The hydrophilic coating also may provide a lubricated surface to facilitate movement through the working channel of medical scope.

An abrasion member 20 having a plurality of prongs 26 is positioned on the distal end of the cannula 12. In this embodiment, the abrasion member 20 is attached separately to the distal end 16 of the cannula 12. The abrasion member 20 may be attached to the cannula 12 by any suitable means, including, but not limited, welding, soldering, heat-setting, and adhesives. One of ordinary skill in the art would understand that the abrasion member 20 may be attached to the distal end of the cannula through other suitable means. Further, the abrasion member 20 may be temporarily attached to the distal end 16 of the cannula 12 or permanently attached to the cannula 12. In alternative embodiments, the abrasion member 20 may be formed integral with the distal end 16 of the cannula 12. The medical device 10 may further include an outer sheath (not shown) disposed about an outer surface of the cannula 12. The outer sheath may be configured to maintain the prongs 26 of the abrasion member 20 in a compressed configuration prior to deployment of the device.

Referring to FIG. 2, the abrasion member 20 comprises a first section 22 and a second section 24. The first section 22 and the second section 24 of the abrasion member 20 each comprise of a plurality of prongs 26. In the first section, the plurality of prongs 26 extends radially outward from the distal end of the cannula at a predetermined angle. The angle formed by the prongs 26 may be equal to or less than about 90 degrees. The prongs 26 of the second section 24 of the abrasion member 20 are configured to be placed upon a surface of the cannula 12. In some embodiments, the prongs 26 of the second section 24 are positioned within an interior surface of the cannula 12. In other embodiments, the prongs 26 of the second section 24 are positioned on an outer surface of the cannula 12. As shown in the figure, the first section 22 of the abrasion member 20 and the second section 24 of the abrasion member 20 each have five prongs. In this embodiment, the prongs 26 of the abrasion member 20 are formed such that the abrasion member 20 has a generally star shaped configuration. One of ordinary skill in the art would understand that in alternative embodiments, other configurations may be suitable for the abrasion member 20.

The abrasion member 20 may be made from numerous metals and alloys. In one example, the abrasion member 20 comprises a shape-memory material such as a nickel-titanium alloy ("Nitinol"). Moreover, the abrasion member 20 may be formed in a variety of ways to provide a suitable support structure. For example, the abrasion members 20 may be made from a woven wire structure, a laser-cut cannula, individual interconnected rings, or another pattern or design. While one exemplary arrangement is shown in FIG. 2, it will be appreciated that the exact number of prongs 26 may be varied. The prongs 26 of the abrasion member 20 have a plurality of struts 28 which are set at angles relative to each other and are connected by an elongated bent segment 30. In one example, the prongs 26 may be configured in the form of in a zigzag configuration in which the struts are set at angles relative to each other and are connected by a bent segment having a generally pointed configuration.

Figure 3:
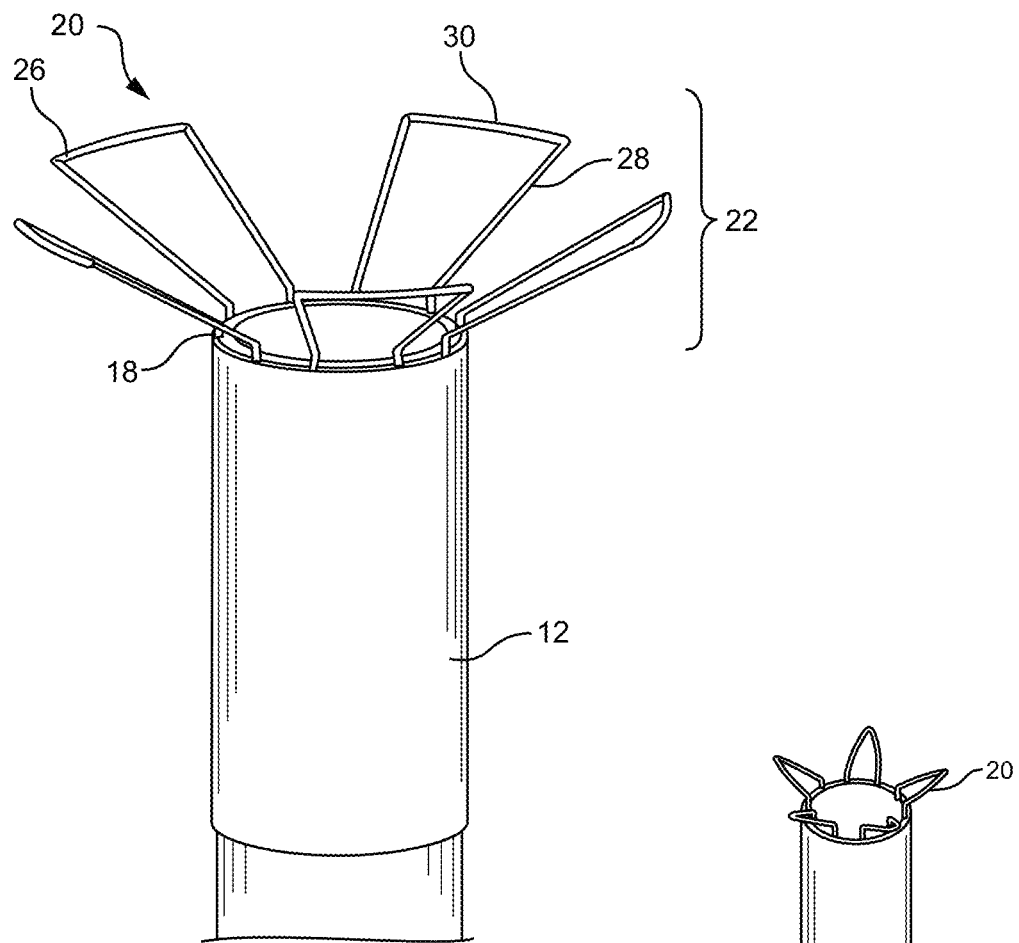
FIG. 3 depicts an alternative embodiment of an abrasion member for use with the endoluminal device of FIG. 1.

FIG. 3 shows the distal end 18 of the cannula 12 with an alternative embodiment of the prongs 26 of the first section 22 of the abrasion member 20. As shown, the prongs 26 of the first section 24 of the abrasion member 20 is non-symmetrical and the struts 28 are generally parallel and are connected by a bent segment 30 having a generally concave arcuate configuration. In alternative embodiments, the bent segment 30 may have a generally straight configuration. The prongs 26 are configured to abrade the urothelium layer of the ureter, such as by scraping or by scratching. In a preferred embodiment, the prongs 26 of the abrasion member 20 will abrade the urothelium layer of the ureter between 1 mm and about 2 mm.

Figure 4:
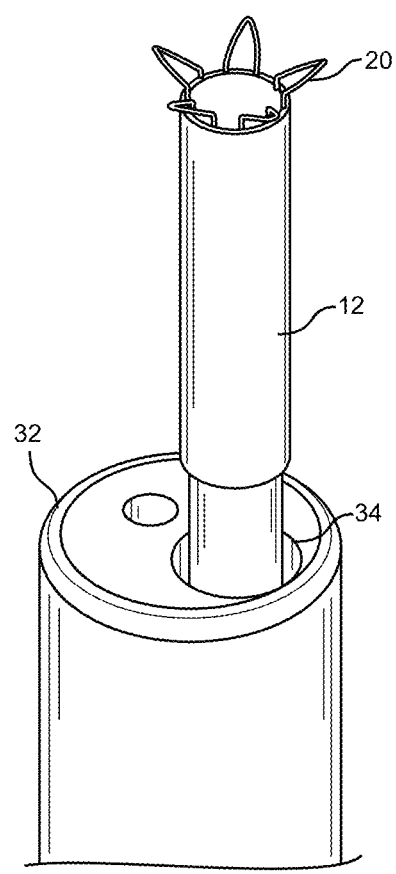
FIG. 4 depicts a scope useful for deploying the endoluminal medical device of FIG. 1.

As shown by FIG. 4, the cannula 12 may be introduced into the ureter through the use of other medical devices, such as a scope 32. The scope includes at least one working or operating channel 34. The working channel 34 extends from the proximal end of the scope to the distal end of the scope. The working channel 34 may be generally tubular and is configured to receive and deliver medical devices into the body of a patient. For example, diagnostic, monitoring, treatment, operating instruments, tools, and accessories, may be passed. The working channel 34 may be manufactured from any suitable biocompatible material. Examples of suitable materials include polyurethane, cellulose acetate, cellulose nitrate, silicone, polyethylene terephthalate, polyamide, polyester, polyorthoester, polyanhydride, polyether sulfone, polycarbonate, polypropylene, high molecular weight polyethylene, and polytetrafluoroethylene. The working channel 34 may be strong and resilient and may comprise a single or multi-layer, and may be composed of or include any material that is flexible, bendable, pliable, elastic, and stretchable (collectively, "flexible"). In alternative embodiments, the cannula 12 may be introduced into the ureter through the use of an access sheath.

Figure 5:
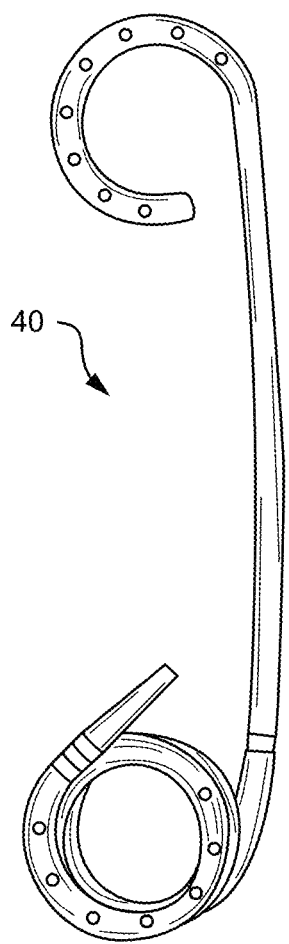
FIG. 5 depicts an ureteral stent useful with the endoluminal medical device embodiment of FIG. 1.

FIG. 5 depicts a stent 40 that may be used in conjunction with the cannula 12. The ureteral stent 40 may be a "double pig-tail" variety, such as those available by Cook Urological Incorporated, Spencer, Ind. The stent is designed to preferably have a length of about 8 cm to about 30 cm and preferably having outer diameters in the range of about 1 mm to about 4 mm. Most preferably, the outer diameters of the stents range from about 1.5 mm to about 3 mm and most preferably the stent will have a wall thickness in the range of about 0.25 mm to about 1 mm. Other suitable ureteral stents may be used with this device. Exemplary embodiments are provided in U.S. Pat. Publication No. 7,550,012, herein incorporated by reference.

One or more pharmacologically active agents, such as medications or drugs, may be placed on the surface of the ureteral stent 40 in order to assist in patient care and comfort. For instance, an antimicrobial drug may help to reduce inflammation and microbial activity in the vicinity of the stent. Analgesics, such as aspirin or other non-steroidal anti-inflammatory drugs, may also be applied to the surface to reduce pain and swelling upon implantation of the stent. Other medications, such as alpha-blockers, may also be used. Alpha-blockers are drugs that block receptors in arteries and smooth muscles. In the urinary tract, alpha-blockers relax the walls of the tract and enhance urinary flow. Examples of suitable alpha-blockers include, but are not limited to, doxazosin, alfuzosin, tamsulosin, prazosin, and terazosin. In a preferred embodiment, the ureteral stent is coated with doxazosin. Any of these pharmacologically active agents is preferably applied in a controlled release so that the beneficial effect of the drug is sustained over a period of at least several days or weeks. This may be especially helpful in the case where the stent will remain in place for a considerable length of time.

In use, a physician may introduce the scope 32 into the ureter over a wire guide and moves the distal end of the scope 32 into the target site. The physician may then insert the cannula 12 into the working channel 34 of the scope 32 and out of the opening of the working channel 34 and into the physician's observation field and working space. During introduction of the cannula 12, the bent sections 28 of the prongs 26 on the first section 22 of the abrasion member 20 are placed into contact with the urothelium layer of the ureter. The physician will reciprocally translate the abrasion member 20 through the ureter in both the proximal and distal direction to cause a controlled abrasion to the urothelium layer of the ureter. After abrading the urothelium, the physician can remove the cannula 12 through the working channel 34 of the scope 34. The physician may introduce a drug eluting ureteral stent 40 into the ureter of the patient using an introducer through the working channel 34 of the scope 32.

Figure 10:
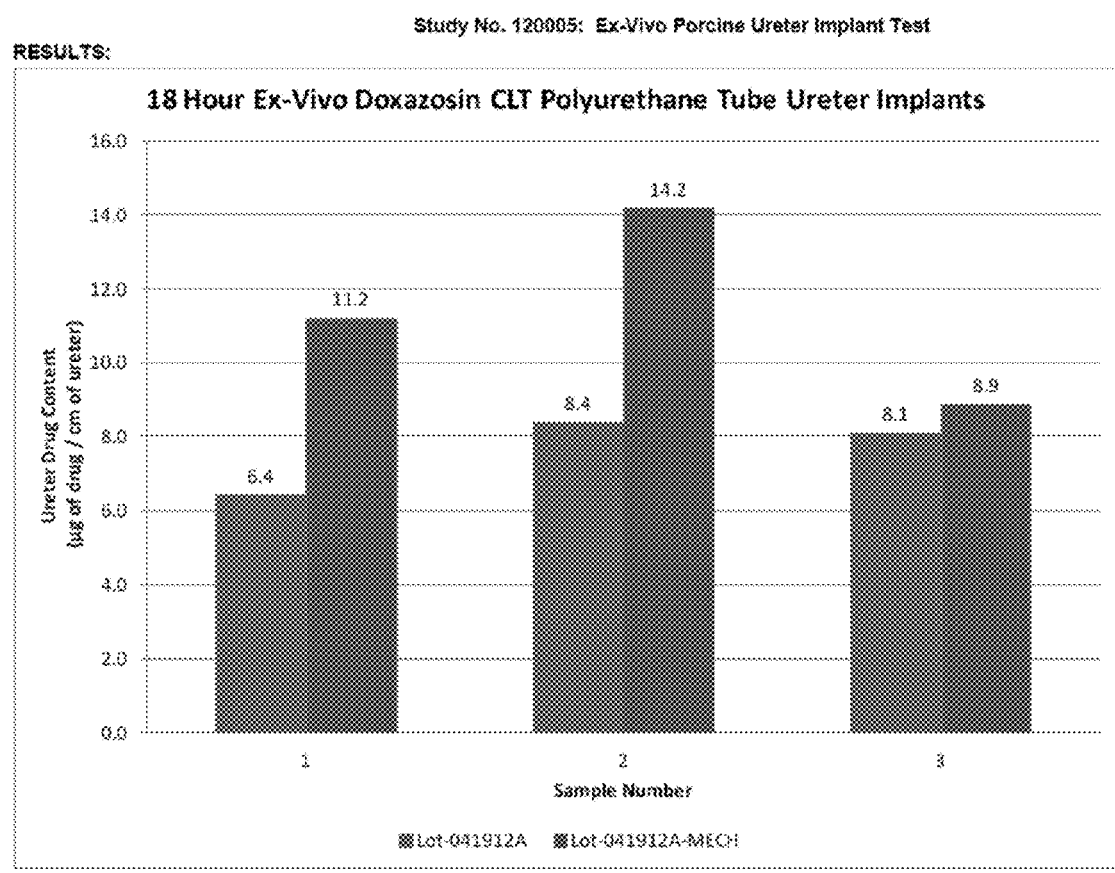
FIG. 10 depicts results from an ex-vivo porcine ureter implant test.

The abrasion caused to the urothelium layer of the ureter of the patient aids in the uptake of the applied drug treatment to the patient. Studies have shown that the urothelium provides a significant barrier to the drug delivery through the ureter. FIG. 10 provides data related to how abrading the urothelium layer of the ureter may aid in the uptake of the applied treatment by the patient. The ex vivo study involved placing a drug eluting stent into porcine ureters obtained from pigs that were slaughtered the same day of the study. Three of the porcine ureters were abraded by scraping the urothelium with a steel cannula prior to implantation of the drug eluting stent. As a control, three porcine ureters were used which were not abraded. The ureters receiving abrasions are referred to in the chart as Lot-041912-MECH and the control ureters are referred to in the chart as Lot-041912.

A 7 cm doxazosin tube was inserted into 9 cm of each ureter and stored for approximately eighteen hours at 37 C in screw capped glass vial which is hydrated with 0.25 ml of phosphate buffered saline ("PBS") solution. The PBS solution generally had a pH of 7.4. Each glass tube was laid down horizontally and the ureter sits directly in the PBS solution. Following the 18 hour period, the doxazosin tubes were removed from the ureters and each ureter was extracted from the glass vials. The ureters were analyzed using high performance liquid chromatography ("HPLC") techniques to determine the amount of drug intake received by each ureter.

As demonstrated by the data (shown in FIG. 10), the ureters receiving abrasions demonstrated significantly increased tissue uptake of the doxazosin drug compared to the control ureters. The abrasions applied to the urothelium layer allows the ureter to receive a greater amount of the drug as opposed ureters that do not receive any abrasions. As such, more of the drug may elute into the ureteral tissue and less will be lost to elution into the urine.

Figure 6:
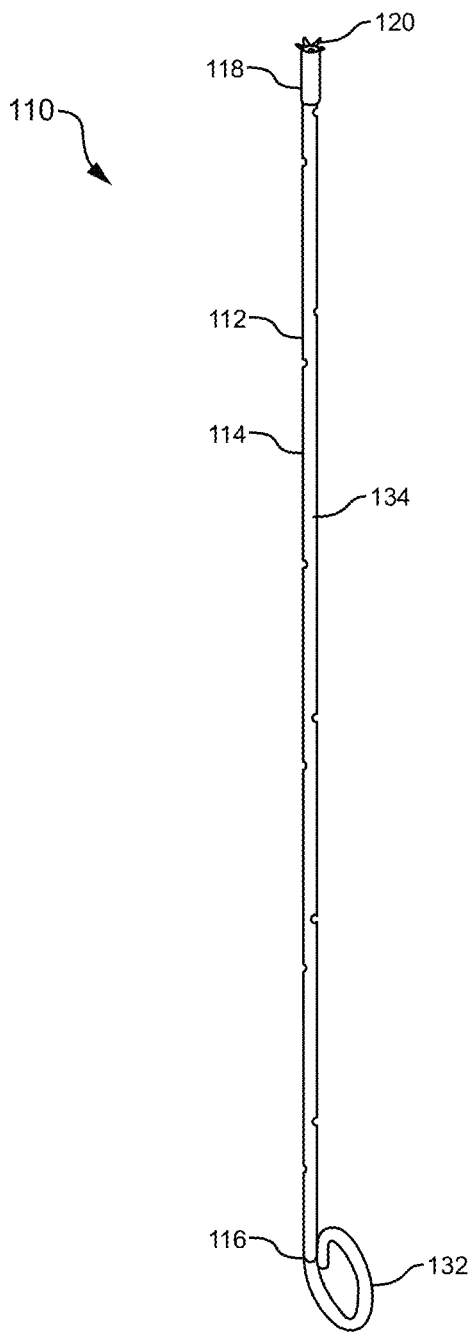
FIG. 6 depicts an alternative embodiment of an endoluminal device having an abrasion member.

FIG. 6 shows an alternative embodiment of an implantable endoluminal device medical device 110. As shown, the medical device 110 comprises a ureteral stent 112 having an elongated tubular body 114 having a proximal end 116 and a distal end 118 and a lumen disposed therethrough. The ureteral stent 112 includes a pigtail shaped retention mechanism 132 on the proximal end 116. Fluid openings or passageways 134 are disposed throughout the length of the ureteral stent 112. The ureteral stent 112 further includes an abrasion member 120. The ureteral stent 112 is produced from flexible material which is preferably elastomeric and containing memory in order that any portion of the stent which is curved will return to its original shape if straightened during the implantation procedure. The polymers or elastomers from which the stent is produced are preferably radiopaque and include polyethylene, silicone; polyurethane; and thermoplastic elastomer. The ureteral stent 112 is designed to preferably have a length of about 8 cm to about 30 cm and preferably having outer diameters in the range of about 1 mm to about 4 mm. Most preferably, the outer diameters of the stents range from about 1.5 mm to about 3 mm and most preferably the stent will have a wall thickness in the range of about 0.25 mm to about 1 mm. The ureteral stent 112 may be introduced using a medical device such as a scope or an access sheath.

One or more pharmacologically active agents, such as medications or drugs, may be placed on the surface of the ureteral stent 112 in order to assist in patient care and comfort. For instance, an antimicrobial drug may help to reduce inflammation and microbial activity in the vicinity of the stent. Analgesics, such as aspirin or other non-steroidal anti-inflammatory drugs, may also be applied to the surface to reduce pain and swelling upon implantation of the stent. Other medications, such as alpha-blockers, may also be used. Alpha-blockers are drugs that block receptors in arteries and smooth muscles. In the urinary tract, alpha-blockers relax the walls of the tract and enhance urinary flow. Examples of suitable alpha-blockers include, but are not limited to, doxazosin, alfuzosin, tamsulosin, prazosin, and terazosin. In a preferred embodiment, the ureteral stent is coated with doxazosin. Any of these pharmacologically active agents is preferably applied in a controlled release so that the beneficial effect of the drug is sustained over a period of at least several days or weeks. This may be especially helpful in the case where the stent will remain in place for a considerable length of time.

Figure 7:
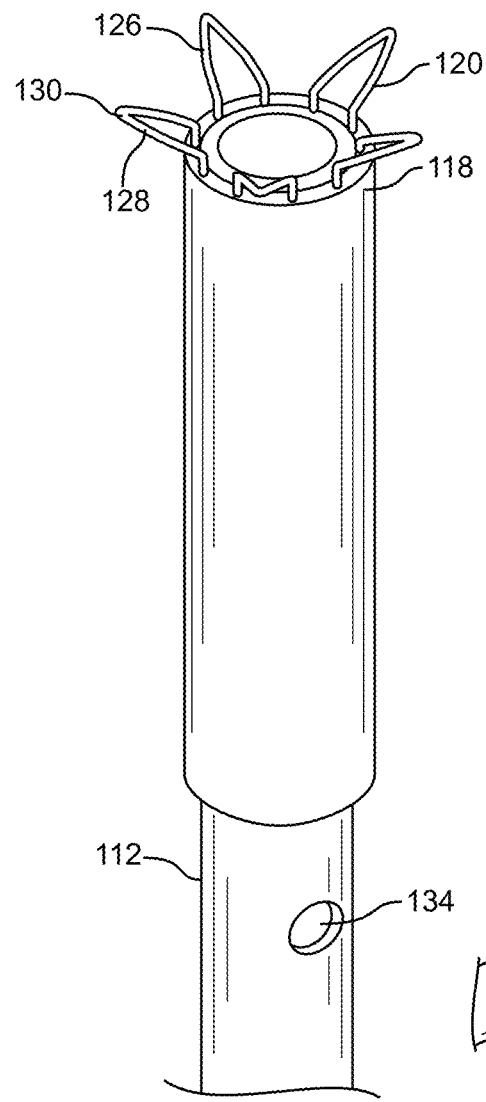
FIG. 7 depicts the distal end of the endoluminal device of FIG. 6.

FIG. 7 shows the distal end 118 of the ureteral stent 112 in greater detail. As shown, the abrasion member 120 includes a plurality of prongs 126. The prongs 126 may comprise a series of struts interconnected by a series of bent segments. In the present embodiment, the abrasion member 120 may be used to provide an abrasion to the urothelium of the ureter during placement of the ureteral stent 112. The abrasion member 120 of the present embodiment may also be used for retention of the ureteral stent 112 within the ureter of the patient. In particular, the abrasion member 120 may be placed distal to the ureteropelvic junction of the patient within the kidney. In alternative embodiments, the stent may include an additional retention member to retain the ureteral stent 112 in the desired position.

Figure 8A:
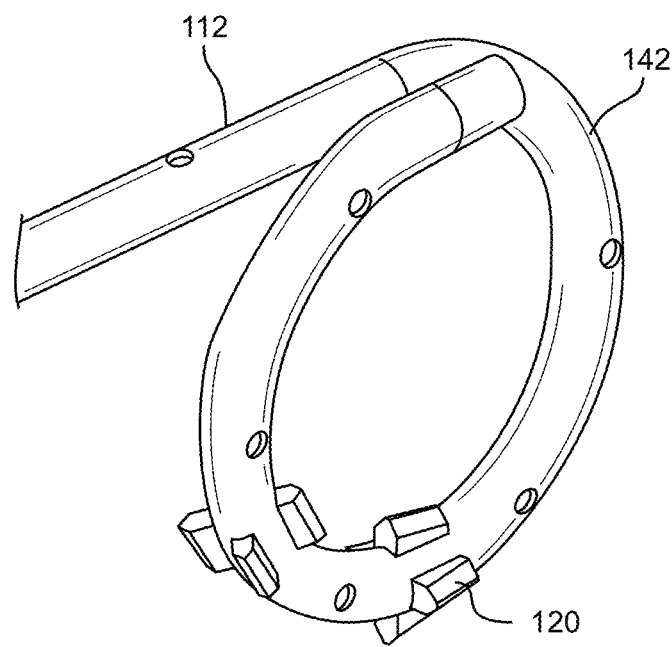
FIGS. 8a-8c depict an alternative embodiments of abrasion members useful with the endoluminal device of FIG. 6.
Figure 8B:
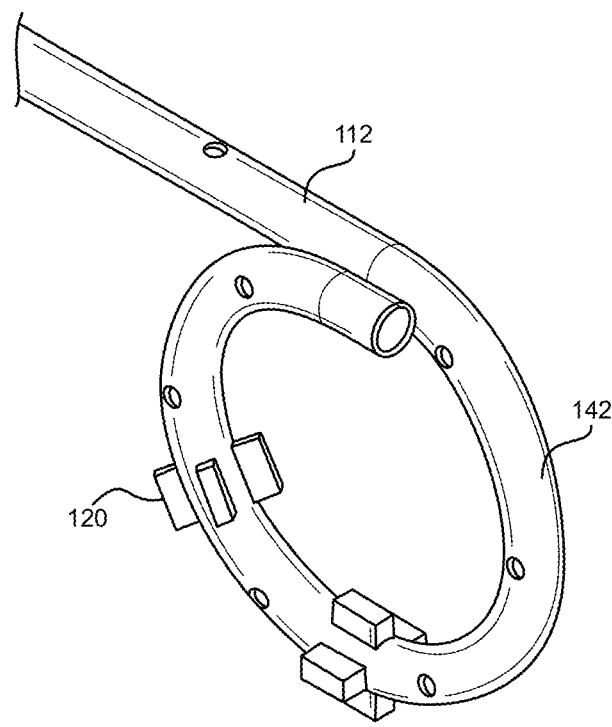
Figure 8C:
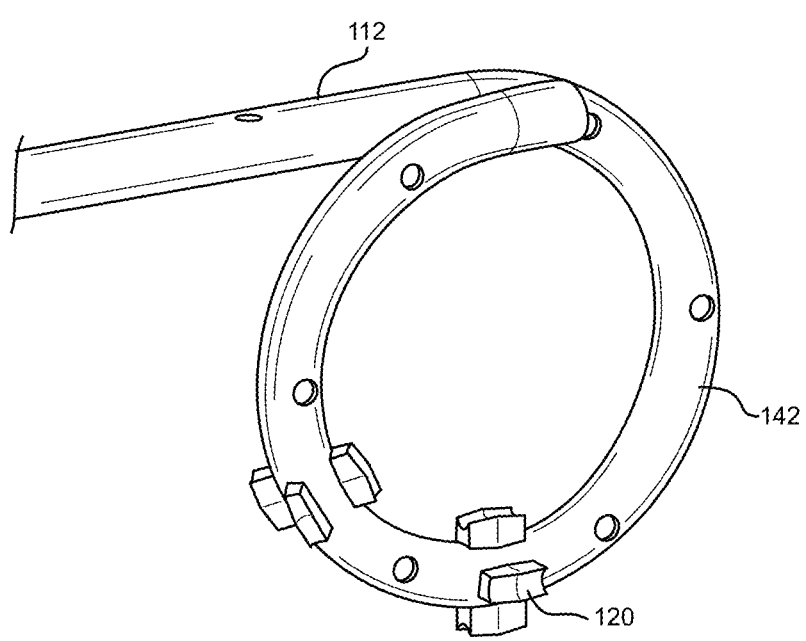

FIGS. 8a-8c show alternative embodiments of the distal end 118 of the ureteral stent 112. In these embodiments, a pigtail shaped retention mechanism 142 is disposed on the proximal end 116 having a plurality of abrasion members 120 disposed on the outer surface of the pigtail shaped retention mechanism 142. In FIG. 8*a*, the abrasion members 120 have a generally pointed configuration. FIG. 8*b* shows the abrasion members 120 having a generally flattened surface. FIG. 8*c* shows the abrasion members 120 have a U-shaped valley or trough. The abrasion members 120 are disposed in eight locations about the surface of the pigtail shaped retention member 142. One of ordinary skill will understand that other configurations may be suitable for the abrasion members 120.

In use, the ureteral stent 112 may be implanted or placed in the ureter by various techniques or procedures. In a preferred embodiment, the ureteral stent 112 is placed over a wire guide and followed by the ureteral stent being placed through a scope and up into the ureter. In another procedure, a wire guide may be first placed through a scope and into the urethra up into the ureter and into the kidney. The stent 112 is then fed onto the wire guide and over the wire guide into the ureter. During introduction of the ureteral stent 112, the bent sections 128 of the prongs 126 on the first section 122 of the abrasion member 120 are placed into contact with the urothelium layer of the ureter. The physician will reciprocally translate the abrasion member 120 through the ureter in both the proximal and distal direction to cause a controlled abrasion to the urothelium layer of the ureter. After abrading the urothelium layer, the physician positions the abrasion member 120 distal to the ureteropelvic junction in the kidney to help retain the ureteral stent 112 within the ureter. A positioning catheter may be used to place the ureteral stent 112 in this procedure where it is stabilized in the bladder and the wire guide is removed from the stent 112. The positioning catheter is then removed along with the wire guide.

FIGS. 9*a* and 9*b* show an alternative embodiment of an endoluminal medical prosthesis 210. As shown, the prosthesis 210 comprises a ureteral stent 212 having an elongated tubular body 214 having a proximal end 216 and a distal end 218 and a lumen disposed therethrough. The ureteral stent 212 includes a pigtail shaped retention mechanism 232 on the proximal end 116 and the distal end 118. The pigtail shaped retention member 232 on the proximal end 218 of the ureteral stent 212 includes an opening. Fluid openings or passageways 234 are disposed throughout the length of the ureteral stent 212. The ureteral stent 212 is designed to preferably have a length of about 8 cm to about 30 cm and preferably having outer diameters in the range of about 1 mm to about 4 mm. Most preferably, the outer diameters of the stents range from about 1.5 mm to about 3 mm and most preferably the stent will have a wall thickness in the range of about 0.25 mm to about 1 mm. A wire 240 having a plurality of abrasion members 220 is removeably positioned within the lumen of the ureteral stent 212 through the opening on the proximal end of the ureteral stent 212. As shown in FIG. 9*b*, the abrasion members 220 on the wire 240 are configured to fit within the fluid openings 234 on the ureteral stent 212. The abrasion members 220 may be distributed throughout the entire length of the wire 240 or in specific portions of the wire 240. In some embodiments, the abrasion members 220 may only be positioned on a distal end of the wire 240 such that they are positioned at a distal portion of the ureteral stent 212

One or more pharmacologically active agents, such as medications or drugs, may be placed on the surface of the ureteral stent 212 in order to assist in patient care and comfort. For instance, an antimicrobial drug may help to reduce inflammation and microbial activity in the vicinity of the stent. Analgesics, such as aspirin or other non-steroidal anti-inflammatory drugs, may also be applied to the surface to reduce pain and swelling upon implantation of the stent. Other medications, such as alpha-blockers, may also be used. Alpha-blockers are drugs that block receptors in arteries and smooth muscles. In the urinary tract, alpha-blockers relax the walls of the tract and enhance urinary flow. Examples of suitable alpha-blockers include, but are not limited to, doxazosin, alfuzosin, tamsulosin, prazosin, and terazosin. In a preferred embodiment, the ureteral stent is coated with doxazosin. Any of these pharmacologically active agents is preferably applied in a controlled release so that the beneficial effect of the drug is sustained over a period of at least several days or weeks. This may be especially helpful in the case where the stent will remain in place for a considerable length of time.

In use, the ureteral stent 212 may be implanted or placed in the ureter by various techniques or procedures. In a preferred embodiment, the ureteral stent 212 is placed over a wire guide and followed by the ureteral stent being placed through a scope and up into the ureter. In another procedure, a wire guide may be first placed through a scope and into the urethra up into the ureter and into the kidney. The ureteral stent 212 is then fed onto the wire guide and over the wire guide into the ureter. During introduction of the ureteral stent 212, the abrasion members 220 positioned on the wire 240 are placed into contact with the urothelium layer of the ureter. The physician will reciprocally translate the abrasion member 220 through the ureter in both the proximal and distal direction to cause a controlled abrasion to the urothelium layer of the ureter. After abrading the urothelium layer the urothelium layer and ureteral stent is placed in the desired position, the physician may remove the wire 240 from the interior of the ureteral stent 212 and physician position the pigtail shaped retention member 232 on the distal end 118 of the ureteral stent 212 distal to the ureteropelvic junction in the kidney to help retain the ureteral stent 212 within the ureter. A positioning catheter may be used to place the ureteral stent 212 in this procedure where it is stabilized in the bladder and the wire guide is removed from the stent 212. The positioning catheter is then removed along with the wire guide.

An endoluminal medical device, comprising, a tubular housing having a proximal end, a distal end, and a lumen longitudinally disposed therethrough; at least one abrasion member comprising a series of struts interconnected by a series of bent segments forming a plurality of prongs attached to the tubular housing, the abrasion member having a first section and a second section; where the prongs of the first section of the abrasion member extend radially outward from the housing, and where the bent segments of the prongs of the first section are configured to engage with the urothelium of the ureter.

Throughout this specification various indications have been given as to preferred and alternative embodiments of the invention. However, the foregoing detailed description is to be regarded as illustrative rather than limiting and the invention is not limited to any one of the provided embodiments. It will be evident to one skilled in the art that modifications and variations may be made without departing from the spirit and scope of the invention. Changes in form and in the proportion of parts, as well as the substitution of equivalents, are contemplated as circumstances may suggest and render expedience; although specific terms have been employed, they are intended in a generic descriptive sense only and not for the purpose of limiting the scope of the invention set forth in the following claims. Moreover, the device is not limited to any specific dimension or material discussed above, nor is the device limited to being used with saline or an image contrast fluid alone.

The invention claimed is:

1. A method of introducing an abrasion to the urothelium layer of the ureter, comprising
providing an endoluminal medical device, the endoluminal device comprising
a tubular housing having a proximal end, a distal end, and a lumen longitudinally disposed therethrough;
at least one abrasion member comprising a series of struts interconnected by a series of bent segments forming a plurality of prongs attached to the tubular housing, the abrasion member having a first section and a second section;
where the prongs of the first section of the abrasion member extend radially outward from the housing
introducing the endoluminal device into the ureter; and
abrading the urothelium layer of the ureter with the endoluminal device.

2. The method of claim 1, wherein the prongs of the first section of the abrasion members have a star shaped configuration.

3. The method of claim 1, wherein the abrasion member comprises a shape-memory material.

4. The method of claim 1, wherein the bent segments of the abrasion member have a circular configuration.

5. The method of claim 1, wherein the prongs of the second section of the abrasion member are disposed on the distal end of the tubular housing.

6. The method of claim 1, further comprising introducing a scope into the ureter prior to introducing the endoluminal device into the ureter.

7. The method of claim 1, further comprising reciprocally translating the abrasion member through the ureter in both the proximal and distal direction.

* * * * *